(12) United States Patent
Seo et al.

(10) Patent No.: US 11,000,344 B2
(45) Date of Patent: May 11, 2021

(54) MEDICAL STAND

(71) Applicants: KOH YOUNG TECHNOLOGY INC., Seoul (KR); INDUSTRY-UNIVERSITY COOPERATION FOUNDATION HANYANG UNIVERSITY ERICA CAMPUS, Ansan-si (KR)

(72) Inventors: Jong Tae Seo, Ansan-si (KR); Byung Ju Yi, Bucheon-si (KR); Jae Hong Woo, Ansan-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-si (KR)

(*) Notice: Subject to any disclaimer, the term of this patent is extended or adjusted under 35 U.S.C. 154(b) by 36 days.

(21) Appl. No.: 16/299,587

(22) Filed: Mar. 12, 2019

(65) Prior Publication Data
US 2019/0209264 A1  Jul. 11, 2019

Related U.S. Application Data (63) Continuation of application No. PCT/KR2017/009972, filed on Sep. 12, 2017.

(30) Foreign Application Priority Data

Sep. 13, 2016 (KR) .................. 10-2016-0118355

(51) Int. Cl.
*A61B 90/00* (2016.01)
*A61B 90/50* (2016.01)
(Continued)

(52) U.S. Cl.
CPC .......... *A61B 90/50* (2016.02); *A61B 1/00149* (2013.01); *A61B 50/26* (2016.02);
(Continued)

(58) Field of Classification Search
CPC .......... A61B 90/50; A61B 34/30; A61B 90/25; G02B 7/001
See application file for complete search history.

(56) References Cited

U.S. PATENT DOCUMENTS

| 5,651,718 A | 7/1997 | Nakamura |
| 6,045,104 A | 4/2000 | Nakamura et al. |

(Continued)

FOREIGN PATENT DOCUMENTS

| JP | 10-272143 | 10/1998 |
| JP | 2009-273714 | 11/2009 |

(Continued)

OTHER PUBLICATIONS

International Search Report for International Application No. PCT/KR25017/009972; dated Dec. 14, 2017.
(Continued)

*Primary Examiner* — Steven M Marsh
(74) *Attorney, Agent, or Firm* — Kile Park Reed & Houtteman PLLC (57) ABSTRACT

A medical stand may include a first link, a second link parallel to the first link, a third link connected between one end of the first link and one end of the second link, a fourth link parallel to the third link and connected between the other end of the first link and the other end of the second link, a mounting arm extending from the other end of the first link, a variable balancing arm connected to at least one of the second link or the third link, a counterweight provided at a distal end of the variable balancing arm, a detector detecting a displacement of at least one of the first link, the
(Continued)

second link, the third link, or the fourth link, and a controller generating the control signal to adjust the center-of-gravity position of the variable balancing arm in accordance with the displacement detected by the detector.

13 Claims, 8 Drawing Sheets

(51) Int. Cl.
| | |
|---|---|
| *B25J 9/00* | (2006.01) |
| *A61B 1/00* | (2006.01) |
| *A61B 50/26* | (2016.01) |
| *B25J 9/10* | (2006.01) |
| *B25J 19/00* | (2006.01) |
| *A61B 17/17* | (2006.01) |

(52) U.S. Cl.
CPC .......... *B25J 9/0018* (2013.01); *B25J 9/0036* (2013.01); *B25J 9/1065* (2013.01); *B25J 19/002* (2013.01); *B25J 19/0016* (2013.01); *A61B 17/17* (2013.01); *A61B 2090/504* (2016.02); *A61B 2090/506* (2016.02)

(56) References Cited

U.S. PATENT DOCUMENTS

| | | | | |
|---|---|---|---|---|
| 7,942,378 | B2* | 5/2011 | Nakamura | A61B 90/50 248/564 |
| 8,006,850 | B2* | 8/2011 | Rotheisler | F16M 11/10 212/196 |
| 8,746,634 | B2* | 6/2014 | Rotheisler | F16M 11/2014 248/123.2 |
| 8,910,913 | B2* | 12/2014 | Hirose | A61B 90/50 248/123.11 |
| 10,228,530 | B2* | 3/2019 | Nakamura | A61B 90/25 |
| 10,293,495 | B2* | 5/2019 | Briot | F16M 11/2092 |
| 10,353,165 | B2* | 7/2019 | Yi | F16M 11/38 |
| 2009/0283647 | A1 | 11/2009 | Yasunaga et al. | |
| 2013/0175412 | A1* | 7/2013 | Schutz | G02B 21/24 248/123.2 |
| 2013/0206934 | A1* | 8/2013 | Schutz | F16M 11/046 248/123.2 |
| 2015/0342692 | A1 | 12/2015 | Yi et al. | |
| 2016/0252699 | A1 | 9/2016 | Yi et al. | |

FOREIGN PATENT DOCUMENTS

| | | |
|---|---|---|
| KR | 10-0136955 | 2/1998 |
| KR | 10-2014-0103655 | 8/2014 |
| KR | 10-2014-0138540 | 12/2014 |

OTHER PUBLICATIONS

KR Notice of reason for refusal with English Translation for Korean Application No. 10-2016-0118355; dispatched Oct. 10, 2017.
KR Decision to Grant with English Translation for Korean Application No. 10-2016-0118355; dispatched Dec. 18, 2017.
Jaehong Woo et al.; "Balancing Arm Design for Variable Payload"; The 12th International Conference on Ubiquitous Robots and Ambient Intelligence (URAI 2015); Oct. 28-30, 2015; pp. 279-280.
Jae-Hong Woo, et al.; "Balancing Arm Design for Counter-weight"; The 7th Annual Conference of Korea Society of Medical Robot; Sep. 19, 2015, Seoul City, Republic of Korea.
Jae-Hong Woo, et al.; "Design of Auto Balancing Arm for Variable Payload"; The 11th Korea Robotics Society Annual Conference; Jan. 24-27, 2016; Pyeongchang, Gangwon Province, Republic of Korea.

* cited by examiner

MEDICAL STAND

CROSS-REFERENCE TO RELATED APPLICATION

This application is a Continuation Application of PCT International Application No. PCT/KR2017/009972, filed on Sep. 12, 2017, which claimed the benefit of Korean Patent Application No. 10-2016-0118355, filed on Sep. 13, 2016, the entire content of each of which is hereby incorporated by reference.

TECHNICAL FIELD

The present disclosure relates to a medical stand.

BACKGROUND

A medical stand is a device that helps a user easily move a medical device such as a surgical microscope or a surgical drill to a desired location with relatively little force. Such a medical stand is useful for surgery, which requires high precision and takes a long time, such as otologic surgery (or ear surgery) or the like. A typical medical stand includes a base as a reference point, a medical device mounted on one side of the base, and a counterbalancing part mounted on a side opposite to the one side of the base where the medical device is mounted. The counterbalancing part comprises a counterweight having a predetermined weight or a counter-spring having a predetermined elastic modulus depending on the weight of the medical device mounted on the base.

When the medical stand is used for surgery, the weight of the medical device mounted on one side of the base of the medical stand may be changed during surgery. In this case, the entire weight balance of the medical stand may collapse because the weight of the counterweight of the counterbalancing part mounted on the other side of the base of the medical stand is fixed. In this case, it may be difficult to perform precise surgery using the medical device. Furthermore, in order to restore the collapsed weight balance, there is a need for the user to replace the counterweight or the counter-spring in accordance with the change in the weight of the medical device.

SUMMARY

Various embodiments of the present disclosure provide a medical stand capable of automatically restoring a weight balance in accordance with a weight change of a medical device mounted on a base of a medical stand.

A medical stand according to one embodiment of the present disclosure may include: a first link; a second link parallel to the first link; a third link connected between one end of the first link and one end of the second link; a fourth link connected between the other end of the first link and the other end of the second link, the fourth link being disposed parallel to the third link; a mounting arm extending from the other end of the first link and configured to be equipped with a medical device at a distal end; a variable balancing arm connected to at least one of the second link or the third link, a center-of-gravity position of the variable balancing arm being variable in accordance with a control signal; a counterweight provided at a distal end of the variable balancing arm; a detector configured to detect a displacement of at least one of the first link, the second link, the third link, or the fourth link; and a controller configured to generate the control signal to adjust the center-of-gravity position of the variable balancing arm in accordance with the displacement detected by the detector.

In one embodiment, the variable balancing arm may include a first balancing arm connected to any one of the second link and the third link, a length of the first balancing arm being variable in accordance with the control signal. The first balancing arm may include: a support portion connected to at least one of the second link and the third link; a movable portion coupled to the support portion so as to be movable in a longitudinal direction of the support portion and on which the counterweight is mounted; and a driving part configured to move the movable portion in the longitudinal direction of the support portion.

In one embodiment, the driving part may include: a driving motor provided on the support portion; a lead screw connected to a driving shaft of the driving motor; and a screw nut provided on the movable portion and threaded onto the lead screw.

In one embodiment, the driving part may include: a driving motor provided on the support portion; a ball screw connected to a driving shaft of the driving motor; and a ball nut provided on the movable portion and threaded onto the ball screw.

In one embodiment, the variable balancing arm may include: a first balancing arm connected to any one of the second link and the third link, a length of the first balancing arm being variable in accordance with the control signal; and a second balancing arm connected to the remaining one of the second link and the third link and having a constant length.

In one embodiment, the medical stand may further include: a counter-spring connected to at least one of the third link or the fourth link.

In one embodiment, the medical stand may further include a base configured to install the medical stand at a fixed position. The counter-spring may include a first counter-spring connected at one end of the first counter-spring to the fourth link and connected at the other end of the first counter-spring to the base of the medical stand.

In one embodiment, the counter-spring may further include a second counter-spring connected at one end of the second counter-spring to the third link and connected at the other end of the second counter-spring to the base.

In one embodiment, the controller may be configured to adjust the length of the variable balancing arm based on at least one of a position, a number, or an elastic modulus of the counter-spring.

In one embodiment, the medical stand may further include: a base configured to install the medical stand at a fixed position; and a hinge configured to pivotably connect the second link and the third link and provided on the base.

In one embodiment, the detector may be provided on the hinge to detect a displacement of at least one of the second link and the fourth link.

In one embodiment, the detector may be provided on the hinge to detect an angle between the second link and the fourth link.

In one embodiment, the medical stand may further include: a fifth link parallel to the fourth link; a sixth link configured to connect the fifth link to a connecting portion for connecting the mounting arm, the first link and the fourth link; a seventh link configured to connect the fifth link to a connecting portion for connecting the second link and the fourth link, the seventh link being parallel to the sixth link; an eighth link disposed parallel to the sixth link, the eighth link being connected to a distal end of the mounting arm;

and a ninth link configured to connect the eighth link to a connecting portion for connecting the fifth link and the sixth link.

In one embodiment, the medical stand may further include a base configured to install the medical stand at a fixed position. The seventh link may be fixed to the base.

DETAILED DESCRIPTION

Embodiments of the present disclosure are illustrated for describing the present disclosure. Embodiments of the present disclosure may be carried out in various forms. The present disclosure is not limited to the embodiments described below or to the detailed descriptions of these embodiments.

The term "part" used in these embodiments means a software component or hardware component, such as a field-programmable gate array (FPGA) and an application specific integrated circuit (ASIC). However, a "part" is not limited to software and hardware. It may be configured to be an addressable storage medium or may be configured to run on one or more processors. For example, a "part" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "part" may be combined into a smaller number of components and "parts" or further subdivided into additional components and "parts."

All technical or scientific terms used herein have a meaning that is generally understood by a person having ordinary knowledge in the art to which the present disclosure pertains, unless otherwise specified. The terms used herein are selected only to more clearly illustrate the present disclosure, and are not intended to limit the scope of the present disclosure.

A singular expression may include the plural meaning, unless otherwise mentioned, and the same is applicable for a singular expression stated in the claims.

The terms "first", "second", etc. used herein are used to identify a plurality of components from one another, and are not intended to limit the order or importance of the relevant components.

The expressions "include", "provided with", "have" and the like used herein should be understood as open-ended terms connoting the possibility of inclusion of other embodiments, unless otherwise mentioned in a phrase or sentence including the expressions.

The expression "based on" used herein is used to describe one or more factors that influence a decision, an action of judgment or an operation described in a phrase or sentence including the relevant expression, and this expression does not exclude additional factors influencing the decision, the action of judgment or the operation.

When a certain component is described as "coupled to" or "connected to" another component, this should be understood as meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, like or relevant components are indicated by like reference numerals. Redundant descriptions of identical or relevant components will be omitted.

Figure 1:
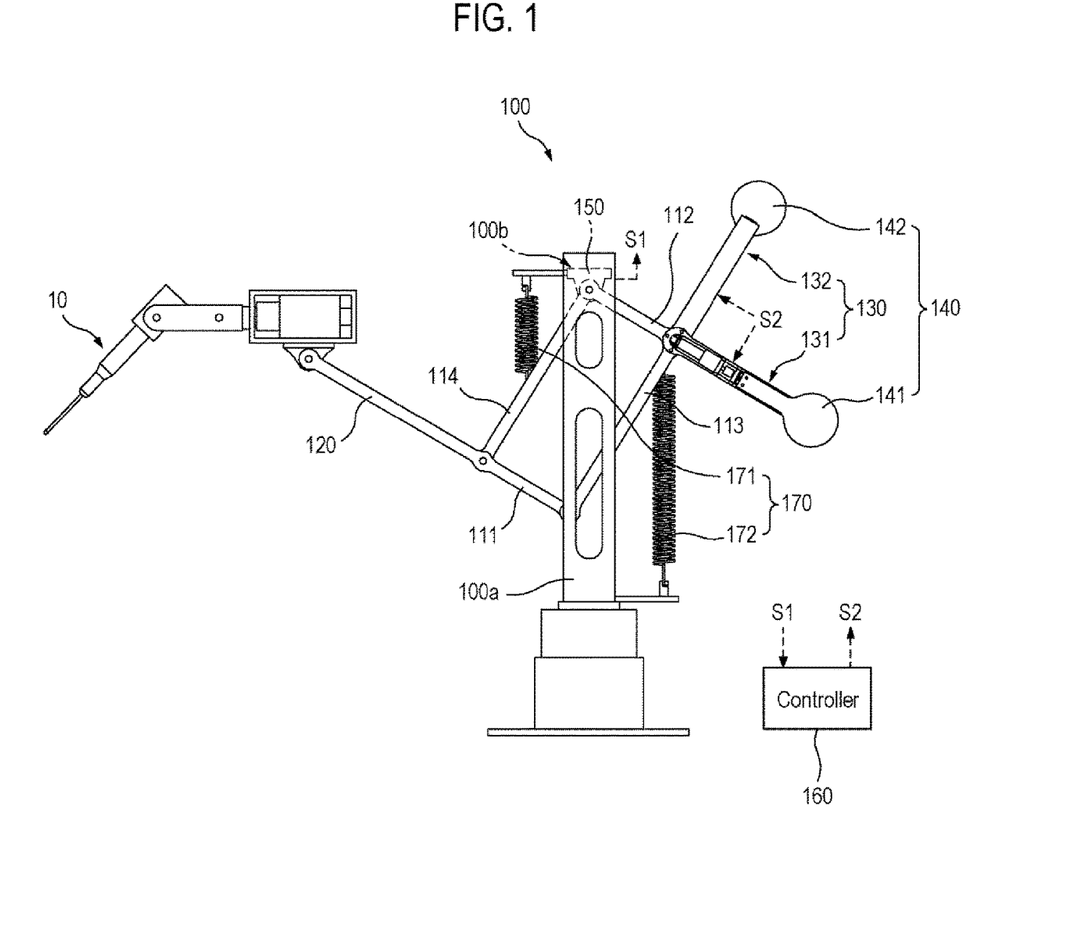
FIG. 1 is a front view of a medical stand according to one embodiment.

As shown in FIG. 1, the medical stand 100 according to one embodiment includes: a first link 111; a second link 112; a third link 113; a fourth link 114; a mounting arm 120; a variable balancing arm 130; a counterweight 140; a detector 150; and a controller 160.

One link of the first to fourth links 111 to 114 may be pivotably connected to another adjacent link. Furthermore, in one embodiment, the entire configuration in which the first to fourth links 111 to 114 are connected may substantially be a parallelogram. Specifically, the first link 111 and the second link 112 may have the same length, and the second link 112 may be disposed parallel to the first link 111. The third link 113 and the fourth link 114 may have the same length, and the fourth link 114 may be disposed parallel to the third link 113. The third link 113 may be connected between one end of the first link 111 and one end of the second link 112. The fourth link 114 may be connected between the other end of the first link 111 and the other end of the second link 112. In this regard, the other ends of the first to fourth links 111 to 114 may represent the ends located on the opposite side of the respective one ends of the first to fourth links 111 to 114. The one end and the other end of any one of the first to fourth links 111 to 114 are not limited to the illustrated embodiment. It should also be understood that the one end and the other end may be located opposite to each other.

The mounting arm 120 may extend from the other end of the first link 111. In one embodiment, the mounting arm 120 may be manufactured separately from the first link 111 and may be coupled to the first link 111. In another embodiment, the mounting arm 120 may be formed integrally with the first link 111 so as to extend along a longitudinal direction of the first link 111 from the other end of the first link 111. A medical device 10 may be mounted at the distal end of the mounting arm 120. The medical stand 100 according to one embodiment may be manufactured and supplied in a state in which the medical device 10 is not mounted thereon. The medical device 10 may include one of various devices used for medical purposes, such as, for example, a surgical microscope and a surgical drill. In one embodiment, the medical device 10 may be replaceably coupled to the distal end of the mounting arm 120. Thus, various types of medical devices may be attached to or detached from the distal end of the mounting arm 120. In one embodiment, the medical device 10 may be fixed to the distal end of the mounting arm 120 so as to have a predetermined orientation. In another embodiment, the medical device 10 may be coupled to the distal end of the mounting arm 120 so as to be pivotable with respect to the mounting arm 120.

The variable balancing arm 130 may be coupled to at least one of the second link 112 or the third link 113. The variable balancing arm 130 is disposed to face the mounting arm 120 with respect to the first to fourth links 111 to 114. The variable balancing arm 130 may be coupled to at least one of the second link 112 or the third link 113 adjacent to each other. The variable balancing arm 130 may be configured so that the center-of-gravity position of the variable balancing arm 130 can be varied in accordance with a control signal transmitted from the controller 160. In one embodiment, the variable balancing arm 130 may only be coupled to one of the second link 112 and the third link 113. For example, the variable balancing arm 130 may include a first balancing arm 131 connected to any one of the second link 112 and the third link 113. A length of the first balancing arm 131 may be variable in accordance with a control signal. In another embodiment, the variable balancing arm 130 may be coupled to each of the second link 112 and the third link 113. For example, the variable balancing arm 130 may include a first balancing arm 131 connected to any one of the second link 112 and the third link 113, and a second balancing arm connected to the remaining one of the second link 112 and the third link 113. A length of the first balancing arm 131 may be variable in accordance with a control signal. A length of the second balancing arm may be constant and not be variable.

As shown in FIG. 1, the variable balancing arm 130 may include a first balancing arm 131 coupled to the second link 112 and a second balancing arm 132 coupled to the third link 113. The variable balancing arm 130 including both the first balancing arm 131 and the second balancing arm 132, which are connected to the second link 112 and the third link 113, respectively, will be described below.

Figure 2:
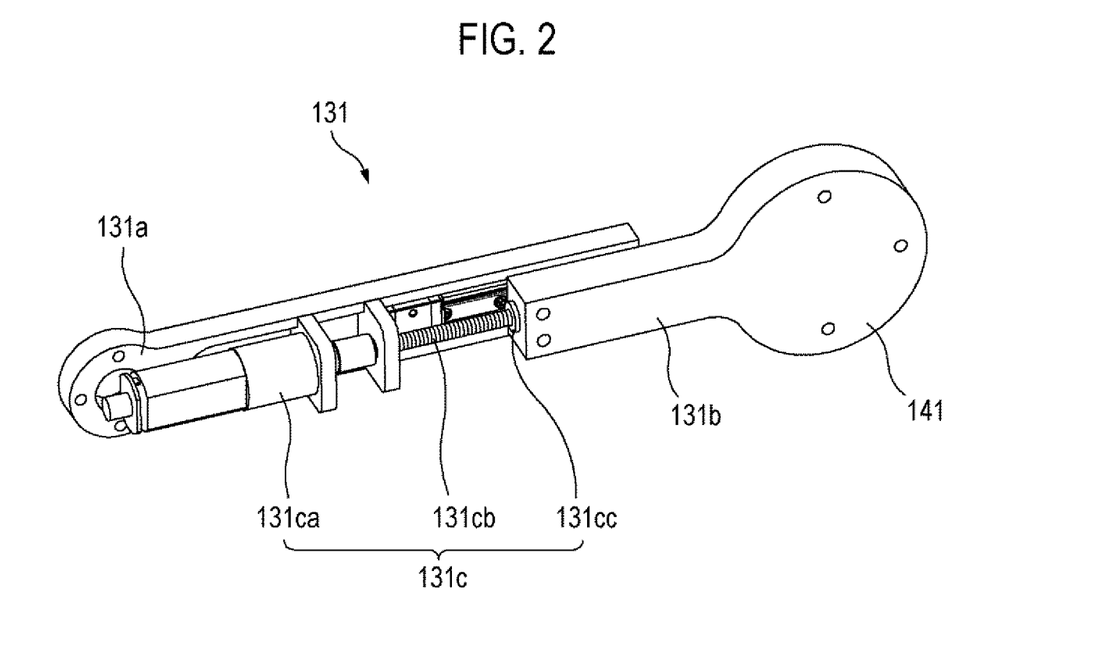
FIG. 2 is a perspective view of a variable balancing arm of the medical stand shown in FIG. 1.

As shown in FIG. 2, the first balancing arm 131 may include a first support portion 131a, a first movable portion 131b, and a first driving part 131c. The first support portion 131a may be connected to the second link 112. In one embodiment, the first support portion 131a may be manufactured separately from the second link 112 and may be coupled to the second link 112. In another embodiment, the first support portion 131a may be integrally formed with the second link 112 so as to extend along a longitudinal direction of the second link 112 from the second link 112. The first movable portion 131b may be coupled to the first support portion 131a so as to be movable in the longitudinal direction of the first support portion 131a. Guide mechanisms complementary to each other may be formed in the first support portion 131a and the first movable portion 131b, respectively, so as to move the first movable portion 131b relative to the first support portion 131a. For example, a guide rail may be formed on the first support portion 131a, while a guide slot corresponding to the guide rail may be formed on the first movable portion 131b. A first counterweight 141 may be mounted on the distal end of the first movable portion 131b. The first driving part 131c may be installed on the first support portion 131a to enable the first movable portion 131b to be movable in the longitudinal direction of the first support portion 131a.

In one embodiment, the second balancing arm 132 may have the same or similar configuration as the first balancing arm 131. Specifically, the second balancing arm 132 may include a second support portion, a second movable portion, and a second driving part, which have structures similar to those of the first support portion 131a, the first movable portion 131b, and the first driving part 131c of the first balancing arm 131. Hereinafter, the detailed description of the elements of the second balancing arm 132 will be omitted under the assumption that the second support portion, the second movable portion, and the second driving part of the second balancing arm 132 correspond to the first support portion 131a, the first movable portion 131b, and the first driving part 131c of the first balancing arm 131. However, the present disclosure is not limited thereto. The second balancing arm 132 may be configured to include elements different from those of the first balancing arm 131.

In one embodiment, as shown in FIG. 2, the first driving part 131c may include a first driving motor 131ca, a first lead screw 131cb, and a first screw nut 131cc. The first driving motor 131ca may be fixed to the first support portion 131a. The first driving motor 131ca may include a driving shaft and may rotate the driving shaft in a forward direction or a reverse direction in accordance with an electrical control signal transmitted from the controller 160. For example, the first driving motor 131ca may include a stepping motor in which the number of rotations or the angle of rotation can be controlled precisely. The first lead screw 131cb may be connected to the driving shaft of the first driving motor 131ca to thereby rotate together with the driving shaft. The first screw nut 131cc may be fixed to the first movable portion 131b and may be threaded onto the first lead screw 131cb. As the driving shaft of the first driving motor 131ca rotates, the first lead screw 131cb may rotate in the forward direction or the reverse direction. The first screw nut 131cc may reciprocate along a longitudinal direction of the first lead screw 131cb together with the first movable portion 131b by the rotation of the first lead screw 131cb.

In another embodiment, the first driving part 131c may include a first driving motor 131ca, a first ball screw, and a first ball nut. The first ball screw and the first ball nut according to this embodiment may have the configuration and function similar to those of the first lead screw 131cb and the first screw nut 131cc according to the aforementioned embodiment. The first ball screw and the first ball nut may be used in place of the first lead screw 131cb and the first screw nut 131cc. Therefore, the detailed description of the first ball screw and the first ball nut will be omitted. In the present disclosure, the first driving part 131c is not limited to the one including the lead screw and the nut, or the one including the ball screw and the ball nut. Other types of mechanisms may be used as the first driving part 131c as long as they can convert the rotational motion of the first driving motor 131ca into the linear reciprocating motion of the first movable portion 131b.

Referring again to FIG. 1, the counterweight 140 may be replaceably installed at the distal end of the variable balancing arm 130. In one embodiment, as shown in FIG. 1, the counterweight 140 may include a first counterweight 141 installed at the distal end of the first balancing arm 131 and a second counterweight 142 installed at the distal end of the second balancing arm 132. A plurality of counterweights 140 having various weights may be provided. The plurality of counterweights 140 may be installed in the medical stand 100 or may be stored in a separate storage box. For example, when the weight of the medical device 10 varies greatly, the counterweight 140 having a corresponding suitable weight may be installed on the variable balancing arm 130.

The detector 150 may be configured to detect a displacement of at least one of the first link 111, the second link 112, the third link 113, or the fourth link 114. The term "displacement" used herein may refer to a change in the position of at least one of the links included in the medical stand, and/or a change in the angle between at least two links. For example, the detector 150 may be configured to detect the degree at which the position of at least one of the first link 111, the second link 112, the third link 113, or the fourth link 114 is changed from a predetermined initial value, or the degree at which the angle between two links of the first link 111, the second link 112, the third link 113, and the fourth link 114 is changed from a predetermined initial value. In one embodiment, the detector 150 may be installed in at least one of the first link 111, the second link 112, the third link 113, or the fourth link 114, or may be installed in a connecting portion or a joint at which two adjacent links are connected. For example, the detector 150 may include a rotary encoder for measuring a rotational angular displacement or a gyro sensor for measuring a position change.

In the embodiment shown in FIG. 1, the controller 160 may be electrically connected to the detector 150, the first driving part 131c of the first balancing arm 131, and the second driving part of the second balancing arm 132. That is, in FIG. 1, the reference character S1 indicated adjacent to the detector 150 and the reference character S2 indicated adjacent to the first and second balancing arms 131 and 132 mean that the components corresponding to these reference characters may be electrically connected to the reference characters S1 and S2 indicated at the controller 160.

The controller 160 generates a control signal to adjust the center-of-gravity position of the variable balancing arm 130 in accordance with the displacement detected by the detector 150. Specifically, the controller 160 may adjust the center-of-gravity position of the variable balancing arm 130 by receiving a corresponding electrical signal in accordance with the displacement detected by the detector 150 and generating a control signal for adjusting the length of the first balancing arm 131 in accordance with the intensity of the received electrical signal. Accordingly, the controller 160 may adjust the center-of-gravity position of the variable balancing arm 130 and the counterweight 140 in response to the weight change amount of the medical device 10.

In one embodiment, the adjustment amount of the length of the variable balancing arm 130 may be determined through an empirical method based on the displacement detected by the detector 150, or may be calculated through mathematical calculation based on the displacement. In this case, the controller 160 may be configured to calculate in real time the adjustment amount of the center-of-gravity position of the variable balancing arm 130 by putting the displacement detected by the detector 150 into a predetermined mathematical equation, and adjust the center-of-gravity position of the variable balancing arm 130 in accordance with the calculated adjustment amount. For example, the center-of-gravity position of the variable balancing arm 130 may be adjusted by changing the length of the first balancing arm 131.

In another embodiment, the controller 160 may be configured so that the displacement is detected in real time by the detector 150 and the center-of-gravity position of the variable balancing arm 130 is adjusted in real time in accordance with the intensity of a corresponding electrical signal. In this case, the controller 160 may be configured to adjust the center-of-gravity position of the variable balancing arm 130 until the displacement detected by the detector 150 becomes zero (i.e., until it is determined that the weight balance of the medical stand 100 is restored). For example, the center-of-gravity position of the variable balancing arm 130 may be adjusted by changing the length of the first balancing arm 131.

The medical stand 100 according to one embodiment may further include a counter-spring 170. For example, the counter-spring 170 may include a coil spring. The counter-spring 170 may be connected to at least one of the third link 113 or the fourth link 114. In one embodiment, the counter-spring 170 may only be connected to one of the third link 113 or the fourth link 114. In another embodiment, the counter-spring 170 may be connected to each of the third link 113 and the fourth link 114. For example, when the weight balance of the medical stand 100 collapses as the weight of the medical device 10 is changed, the counter-spring 170 may restrain the movement of at least one of the third link 113 or the fourth link 114 by an elastic restoration force. That is, when the weight balance of the medical stand 100 collapses, the counter-spring 170 may restrain the movement of at least one of the third link 113 or the fourth link 114 to primarily restore the weight balance of the medical stand 100.

In one embodiment, when the medical stand 100 includes the counter-spring 170, the controller 160 may control the driving of the variable balancing arm 130 based on at least one of the position, number, or elastic modulus of the counter-spring 170 so as to adjust the center-of-gravity position of the variable balancing arm 130. The elastic restoration force of the counter-spring 170 can be determined by the position, number and elastic modulus of the counter-spring 170. When the medical stand 100 according to one embodiment includes the counter-spring 170, the adjustment amount of the center-of-gravity position of the variable balancing arm 130 may be reduced as compared with a case where the medical stand 100 does not include the counter-spring 170. After the counter-spring 170 primarily restores the weight balance of the medical stand 100 by the elastic restoration force of the counter-spring 170, or simultaneously with the primary restoration of the weight balance, the controller 160 may secondarily (or additionally) restore the weight balance of the medical stand 100 by adjusting the center-of-gravity position of the variable balancing arm 130. Since the medical stand 100 includes both the variable balancing arm 130 and the counter-spring 170 as described above, it is possible to effectively restore the weight balance of the medical stand 100 even though the weight of the medical device 10 is greatly changed.

In one embodiment, the counter-spring 170 may include a first counter-spring 171 connected to the fourth link 114 and a second counter-spring 172 connected to the third link 113. The first counter-spring 171 may be connected at one end to the fourth link 114 and at the other end to the base 100a of the medical stand 100. The first counter-spring 171 may suppress the movement of the fourth link 114 when the weight of the medical device 10 is changed. In this regard, the base 100a may be a part of the body of the medical stand 100 and may be fixedly mounted to an external component such as a floor or a wall of a place where the medical stand 100 is installed. In addition, the mounting position of the base 100a is not limited to the position of the illustrated embodiment. The base 100a may be mounted at any position of other components of the medical stand 100. The second counter-spring 172 may be connected at one end to the third link 113 and at the other end to the base 100a. The second counter-spring 172 may suppress the movement of the third link 113 when the weight of the medical device 10 is changed. One end of the first counter-spring 171 may be connected to the fourth link 114 by a wire, while one end of the second counter-spring 172 may be connected to the third link 113 by a wire.

In another embodiment, the position of the fourth link 114 to which one end of the first counter-spring 171 is connected is configured to be variable, so that the magnitude of the elastic restoration force of the first counter-spring 171 can be adjusted. In addition, the position of the third link 113 to which one end of the second counter-spring 172 is connected is configured to be variable, so that the magnitude of the elastic restoration force of the second counter-spring 172 can be adjusted.

The medical stand 100 according to one embodiment may further include a hinge 100b installed on the base 100a. The hinge 100b may be fixedly installed on the base 100a and connect the other end of the second link 112 and the fourth link 114 so as to be pivotable relative to each other. In one embodiment, the detector 150 may be installed in the hinge 100b to detect a displacement of at least one of the second link 112 or the fourth link 114. For example, the detector 150 may detect a displacement where the position of at least one of the second link 112 or the fourth link 114 is changed from a predetermined initial position. In another embodiment, the detector 150 may be installed in the hinge 100b to detect an angle between the second link 112 and the fourth link 114. For example, the detector 150 may detect a displacement where the angle between the second link 112 and the fourth link 114 is changed from a predetermined initial value.

Figure 3:
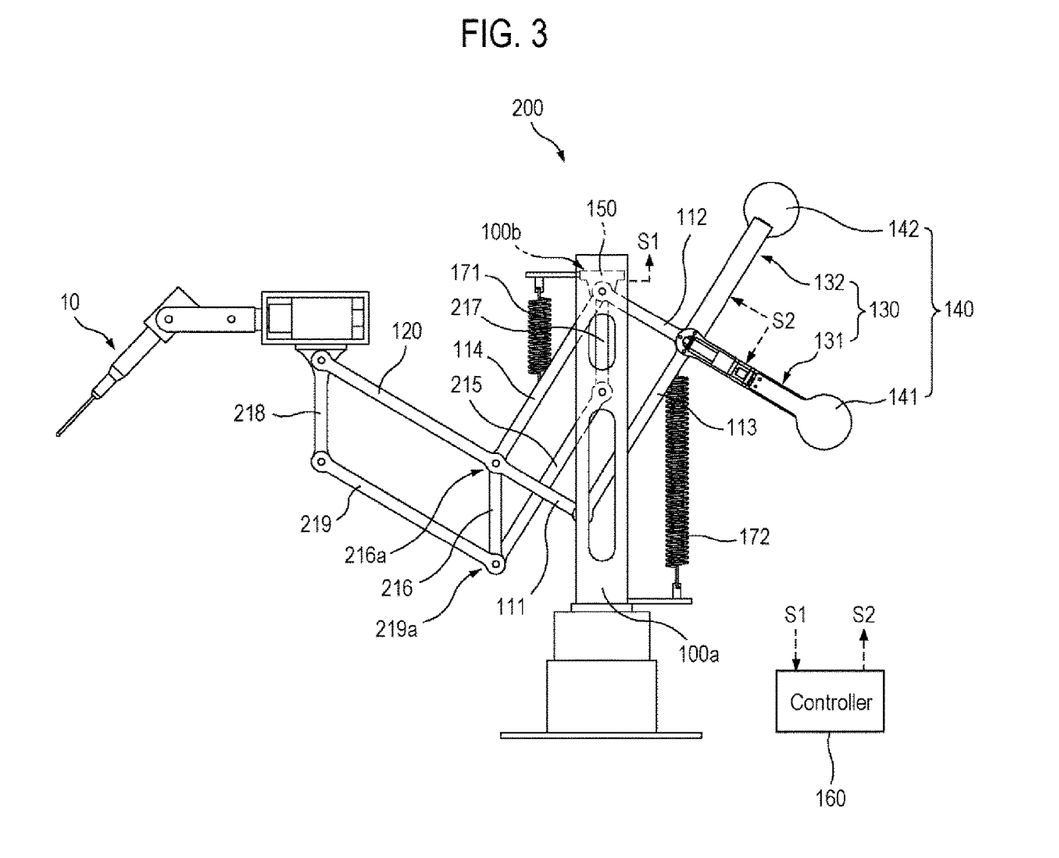
FIG. 3 is a front view of a medical stand according to another embodiment.

FIG. 3 is a front view of a medical stand 200 according to another embodiment. As shown in FIG. 3, the medical stand 200 may include: a first link 111; a second link 112; a third link 113; a fourth link 114; a mounting arm 120; a variable balancing arm 130; a counterweight 140; a detector 150; a controller 160; a fifth link 215; a sixth link 216; a seventh link 217; an eighth link 218; and a ninth link 219. In the medical stand 200 according to this embodiment, the same elements as those of the medical stand 100 according to the embodiment shown in FIG. 1 will be denoted by the same reference numerals, and the detailed description thereof will be omitted. Hereinafter, the fifth to ninth links 215 to 219 will be described in more detail.

The fifth link 215 may be disposed between the third link 113 and the fourth link 114 so as to be parallel to the third link 113 and the fourth link 114. The sixth link 216 may connect the fifth link 215 to a connecting portion 216a that connects the mounting arm 120, the first link 111, and the fourth link 114. The seventh link 217 may connect the fifth link 215 to a connecting portion 217a (see FIG. 4) that connects the second link 112 and the fourth link 114. The seventh link 217 and the eighth link 218 may be disposed parallel to the sixth link 216. The eighth link 218 may be connected to the distal end of the mounting arm 120. The ninth link 219 may connect the eighth link 218 to a connecting portion 219a that connects the fifth link 215 and the sixth link 216. The ninth link 219 may be disposed parallel to the mounting arm 120.

Figure 4:
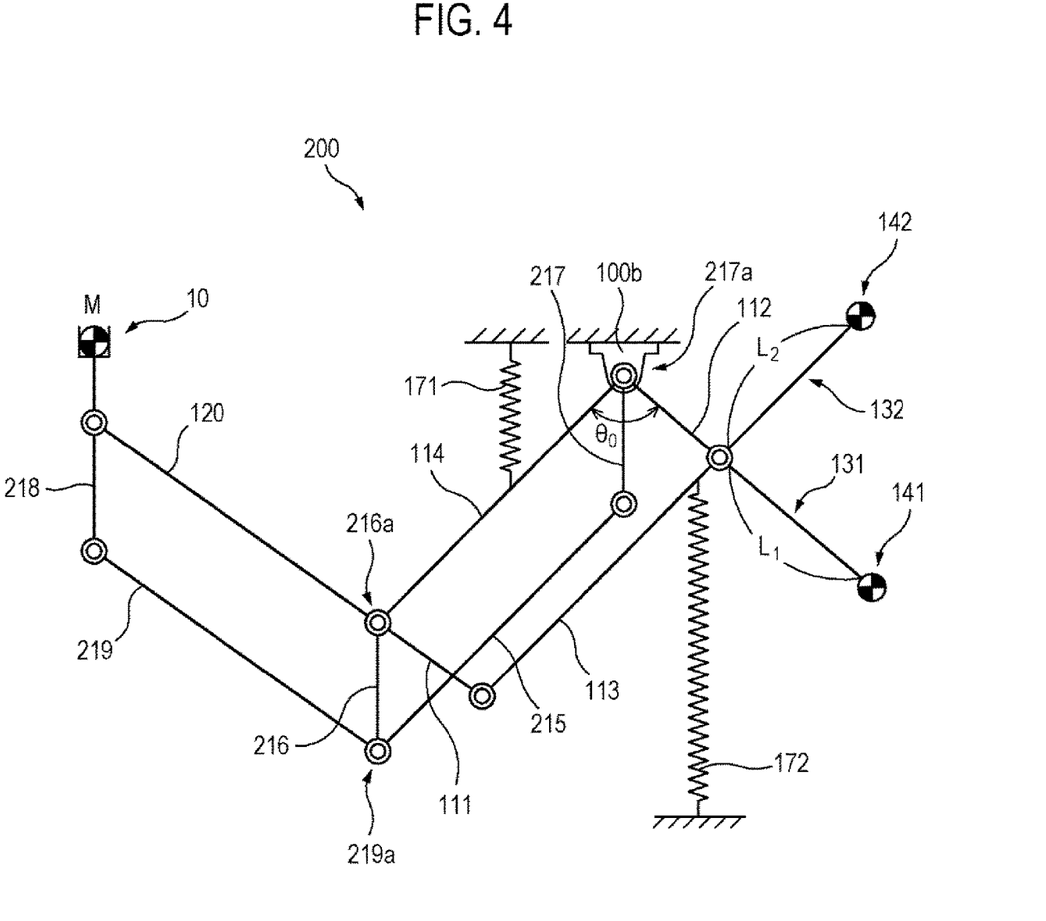
FIG. 4 is a diagram schematically showing the structure of the medical stand shown in FIG. 3.

As shown in FIG. 3, the entire shape of the fourth link 114, the fifth link 215, the sixth link 216, and the seventh link 217 forms a parallelogram. The entire shape of the mounting arm 120, the sixth link 216, the eighth link 218, and the ninth link 219 also forms a parallelogram. That is, the two structures having a parallelogram shape configured as described above may share the sixth link 216. In one embodiment, the seventh link 217 may be fixed to a base 100a of the medical stand 200. As shown in FIGS. 3 and 4, when the seventh link 217 is fixed to the base 100a, the eighth link 218 may be kept parallel to the seventh link 217 at all times. With this configuration, the medical device 10 mounted on the eighth link 218 (or the mounting arm 120) may always have the same orientation.

Hereinafter, a balance restoration method for the medical stand 200 will be described with reference to FIGS. 4 to 8. In the medical stand 200 described below, it is assumed that: the variable balancing arm 130 includes the first and second balancing arms 131 and 132; the counter-spring 170 includes the first and second counter-springs 171 and 172; and the hinge 100b is disposed at the connecting portion 217a for connecting the second link 112 and the fourth link 114. Furthermore, it is assumed that: the detector 150 is installed on the hinge 100b to detect the angle between the second link 112 and the fourth link 114; and the seventh link 217 is fixed to the base 100a.

FIG. 4 is a diagram schematically showing the structure of the medical stand 200 shown in FIG. 3. If it is assumed that: the weight of the medical device 10 is M; the length of the first balancing arm 131 is $L_1$; and the length of the second balancing arm 132 is $L_2$, the medical stand 200 maintains a weight balance in a state in which the angle between the second link 112 and the fourth link 114 is $\theta_0$.

Figure 5:
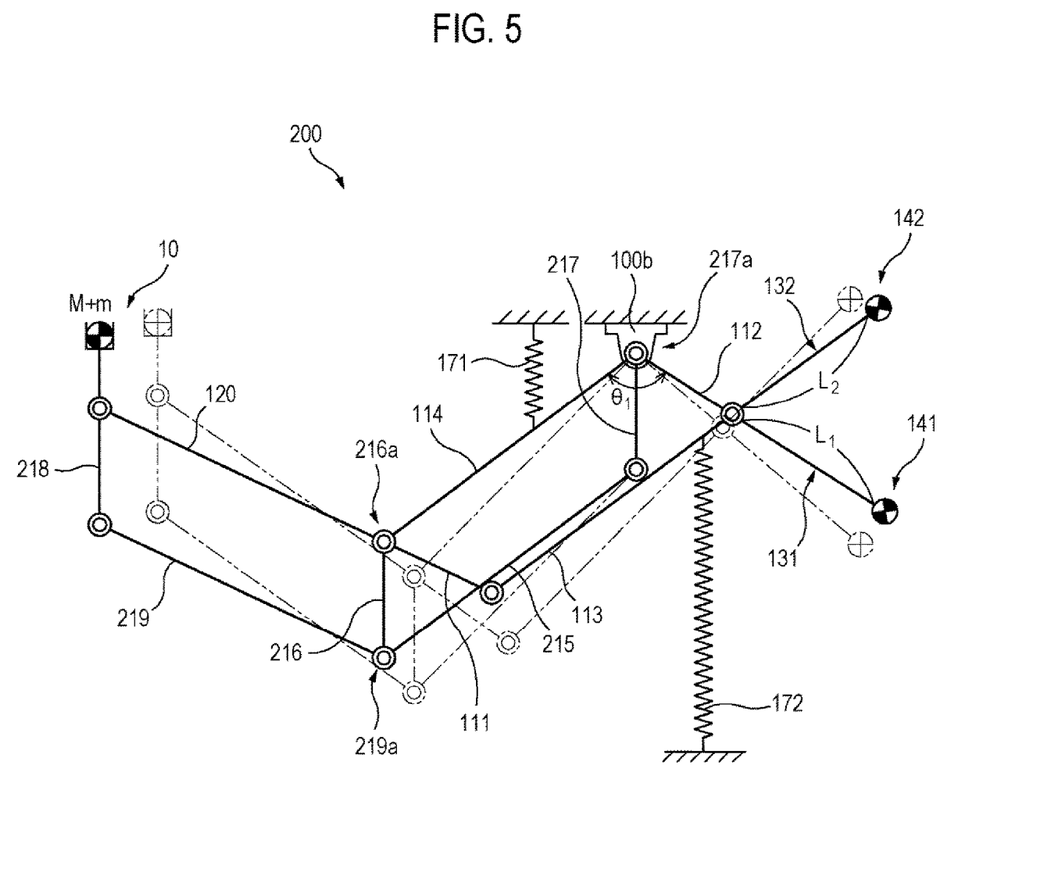
FIG. 5 is a diagram showing one example of a state in which the weight balance of the medical stand shown in FIG. 4 has collapsed.

FIG. 5 is a diagram showing one example of a state in which the weight balance of the medical stand 200 shown in FIG. 4 has collapsed. As shown in FIG. 5, if the weight M of the medical device 10 increases to M+m, the medical device 10 may be moved downward such that the weight balance of the medical stand 200 may be changed from the state shown in FIG. 4 to the state shown in FIG. 5. In this case, the angle between the second link 112 and the fourth link 114 may be changed from $\theta_0$ to $\theta_1$. The detector 150 may detect the change amount of the angle ($\Delta\theta=\theta_1-\theta_0$) to thereby generate an electrical signal corresponding to the change amount of the angle. The controller 160 may control the first driving part 131c of the first balancing arm 131 and the second driving part of the second balancing arm 132 so as to increase the length of the first balancing arm 131 and the second balancing arm 132 in accordance with the intensity of the electrical signal received from the detector 150.

Figure 6:
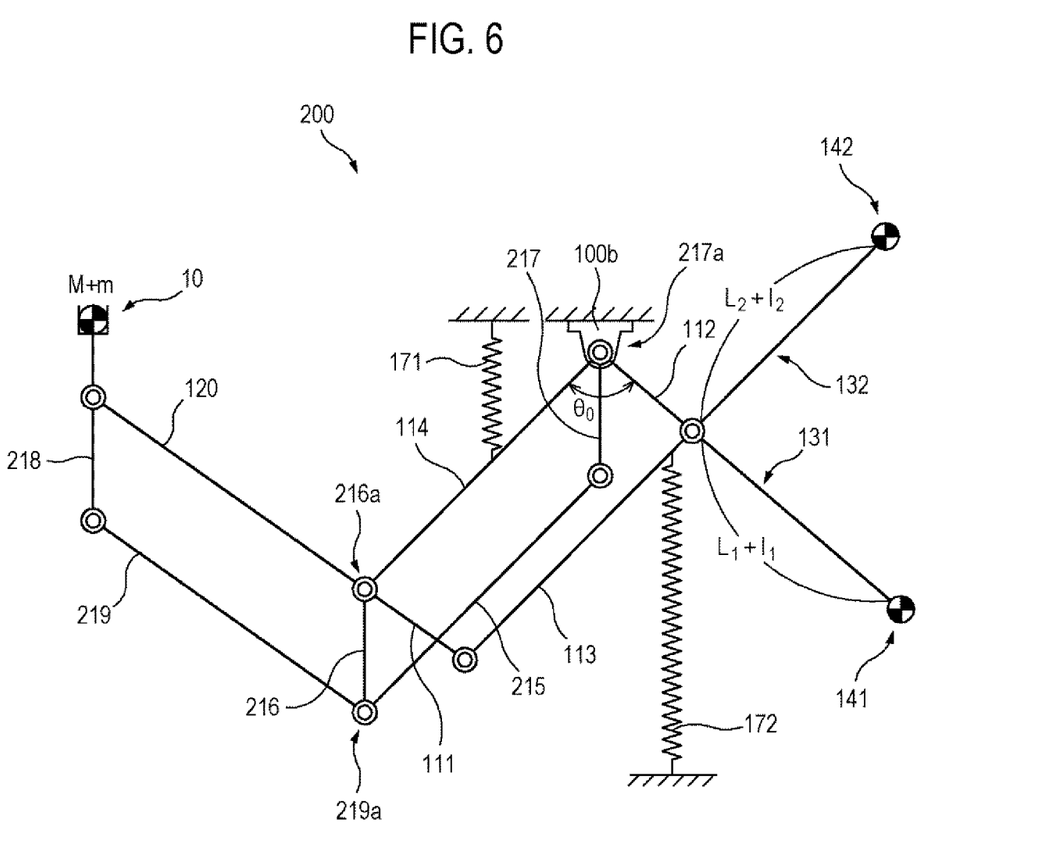
FIG. 6 is a diagram showing a state in which the weight balance of the medical stand shown in FIG. 5 is restored.

FIG. 6 is a diagram showing a state in which the weight balance of the medical stand 200 shown in FIG. 5 is restored. In one embodiment, the controller 160 may calculate the rotation direction and the rotation amount of the driving shaft of the first driving motor 131ca in accordance with the intensity of the electrical signal detected by the detector 150. When the driving shaft of the first driving motor 131ca is rotated by the calculated rotation amount in the forward direction, the first lead screw 131cb (or the first ball screw) may rotate. As the first lead screw 131cb rotates, the first movable portion 131b coupled to the first screw nut 131cc (or the first ball nut) may be moved along the longitudinal direction of the first support portion 131a. Therefore, the length of the first balancing arm 131 may be increased by $l_1$, and the total length of the first balancing arm 131 may be set to $L_1+l_1$. The controller 160 may perform control so as to adjust the length of the second balancing arm 132 through a method similar to that applied to the first balancing arm 131. Accordingly, the length of the second balancing arm 132 may be increased by 12, and the total length of the second balancing arm 132 may be set to $L_2+l_2$. As a result, the weight balance of the medical stand 200 may be changed from the state shown in FIG. 5 to the state shown in FIG. 6. In this way, the weight balance of the medical stand 200 may be restored. As a result, the positions of the respective links and the medical device 10 shown in FIG. 6 may be restored to the same positions as the respective links and the medical device 10 shown in FIG. 4. Meanwhile, the lengths of the first and second balancing arms 131 and 132 shown in FIG.

6 may be longer than the lengths of the first and second balancing arms 131 and 132 shown in FIG. 4.

Figure 7:
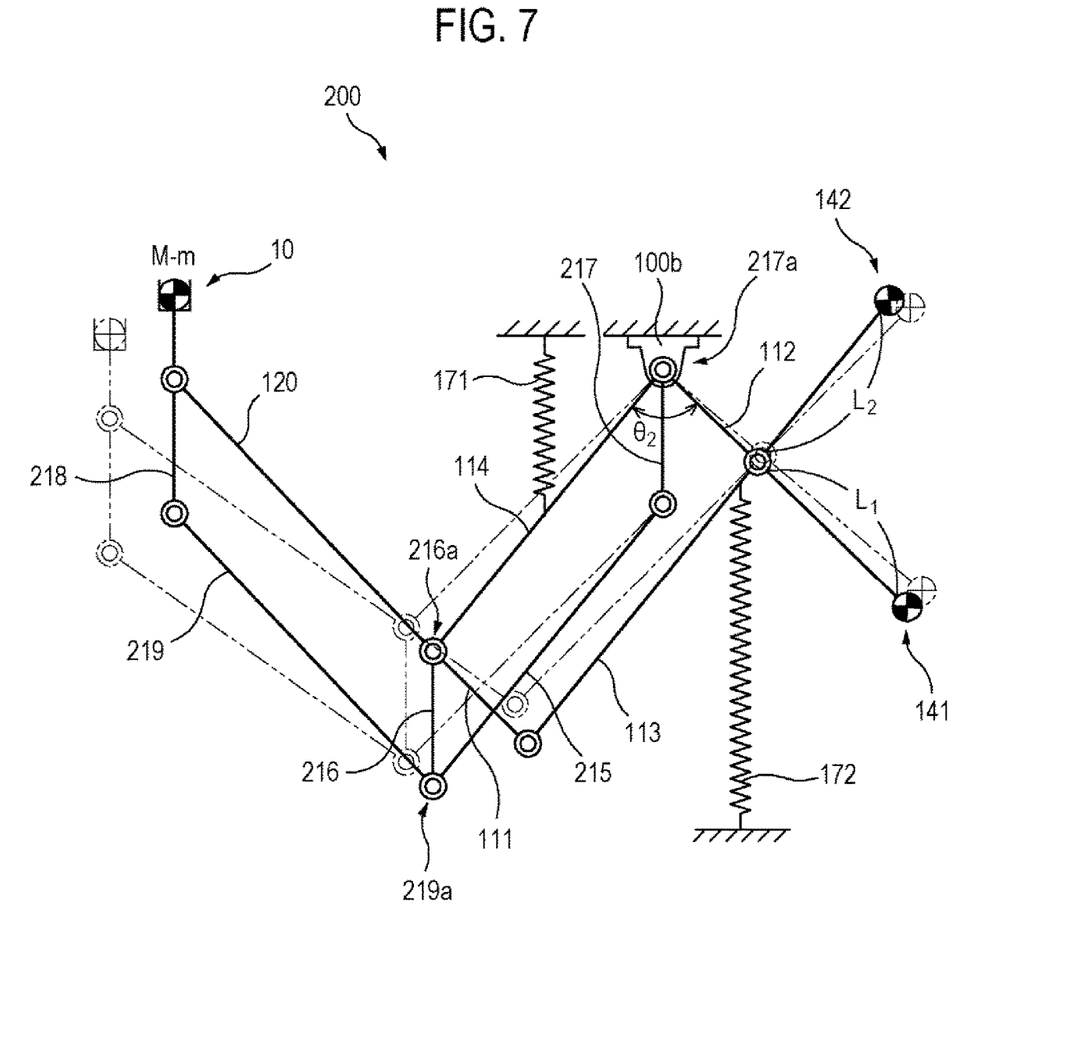
FIG. 7 is a diagram showing another example of the state in which the weight balance of the medical stand shown in FIG. 4 has collapsed.

FIG. 7 is a diagram showing another example of a state in which the weight balance of the medical stand 200 shown in FIG. 4 has collapsed. As shown in FIG. 7, if the weight M of the medical device 10 decreases to M−m, the medical device 10 may be moved upward such that the weight balance of the medical stand 200 may be changed from the state shown in FIG. 4 to the state shown in FIG. 7. In this case, the angle between the second link 112 and the fourth link 114 may be changed from $\theta_0$ to $\theta_2$. The detector 150 may detect the change amount of the angle ($\Delta\theta=\theta_2-\theta_0$) to thereby generate an electrical signal corresponding to the change amount of the angle. The controller 160 may control the first driving part 131c of the first balancing arm 131 and the second driving part of the second balancing arm 132 so as to decrease the length of the first balancing arm 131 and the second balancing arm 132 in accordance with the intensity of the electrical signal received from the detector 150.

Figure 8:
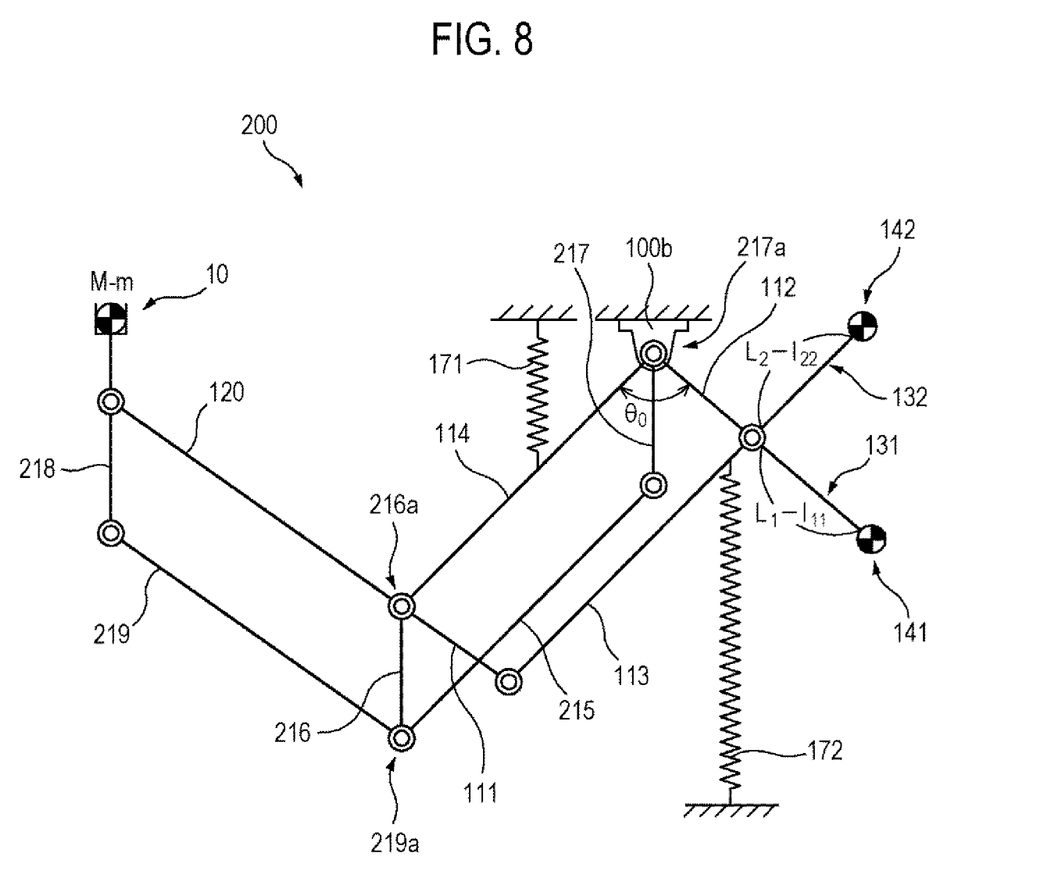
FIG. 8 is a diagram showing a state in which the weight balance of the medical stand shown in FIG. 7 is restored.

FIG. 8 is a diagram showing a state in which the weight balance of the medical stand 200 shown in FIG. 7 is restored. In one embodiment, the controller 160 may calculate the rotation direction and the rotation amount of the driving shaft of the first driving motor 131ca in accordance with the intensity of the electrical signal detected by the detector 150. When the driving shaft of the first driving motor 131ca is rotated by the calculated rotation amount in the reverse direction, the first lead screw 131cb (or the first ball screw) may rotate. As the first lead screw 131cb rotates, the first movable portion 131b coupled to the first screw nut 131cc (or the first ball nut) may be moved along the longitudinal direction of the first support portion 131a. Therefore, the length of the first balancing arm 131 may be decreased by $l_{11}$, and the total length of the first balancing arm 131 may be set to $L_1-l_{11}$. The controller 160 may perform control so as to adjust the length of the second balancing arm 132 through a method similar to that applied to the first balancing arm 131. Accordingly, the length of the second balancing arm 132 may be decreased by $l_2$, and the total length of the second balancing arm 132 may be set to $L_2-l_{22}$. As a result, the weight balance of the medical stand 200 may be changed from the state shown in FIG. 7 to the state shown in FIG. 8. In this way, the weight balance of the medical stand 200 may be restored. The positions of the respective links and the medical device 10 shown in FIG. 8 may be restored to the same positions as the respective links and the medical device 10 shown in FIG. 4. Meanwhile, the lengths of the first and second balancing arms 131 and 132 shown in FIG. 8 may be shorter than the lengths of the first and second balancing arms 131 and 132 shown in FIG. 4.

The present disclosure is not limited to the above-described rotation direction (the forward direction or the reverse direction) of the driving shaft. The rotation direction of the driving shaft may be changed appropriately depending on the installation direction and position of the driving motor. In the case where the variable balancing arm 130 includes only one of the first balancing arm 131 and the second balancing arm 132, the adjustment amount of the center-of-gravity position of the variable balancing arm 130 may be set to be larger than the adjustment amount of the center-of-gravity position of each variable balancing arm in the case where the variable balancing arm 130 includes both the first balancing arm 131 and the second balancing arm 132.

While the foregoing methods have been described with respect to particular embodiments, these methods may also be implemented as computer-readable code on a computer-readable recording medium. The computer-readable recording medium includes any kind of data storage devices that can be read by a computer system. Examples of the computer-readable recording medium includes ROM, RAM, CD-ROM, magnetic tape, floppy disk, optical data storage device and the like. Also, the computer-readable recording medium can be distributed to the computer systems which are connected through a network so that the computer-readable code can be stored and executed in a distributed manner. Further, the functional programs, codes and code segments for implementing the foregoing embodiments can easily be inferred by programmers in the art to which the present disclosure pertains.

According to the medical stand in accordance with one embodiment, the displacement of the link due to the change in the weight of the medical device mounted on the medical stand is detected by the detector, and the length of the variable balancing arm is adjusted based on the displacement of the link detected by the detector. Therefore, it is possible to automatically restore the overall weight balance of the medical stand by adjusting the length of the variable balancing arm in accordance with the change in the weight of the medical device.

Although the technical spirit of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that that such substitutions, modifications and changes are intended to fall within the scope of the appended claims.

What is claimed is:

1. A medical stand, comprising:
    a first link;
    a second link parallel to the first link;
    a third link connected between one end of the first link and one end of the second link;
    a fourth link connected between the other end of the first link and the other end of the second link, the fourth link being parallel to the third link;
    a mounting arm extending from the other end of the first link and configured to be equipped with a medical device at a distal end;
    a variable balancing arm connected to at least one of the second link or the third link, a center-of-gravity position of the variable balancing arm being variable in accordance with a control signal;
    a counterweight provided at a distal end of the variable balancing arm;
    a detector configured to detect a displacement of at least one of the first link, the second link, the third link or the fourth link;
    a controller configured to generate the control signal to adjust the center-of-gravity position of the variable balancing arm in accordance with the displacement detected by the detector; and
    a counter-spring connected to at least one of the third link or the fourth link.

2. The medical stand of claim 1, wherein the variable balancing arm includes a first balancing arm connected to any one of the second link and the third link, a length of the first balancing arm being variable in accordance with the control signal, and
    wherein the first balancing arm includes:

a support portion connected to at least one of the second link and the third link;

a movable portion coupled to the support portion so as to be movable in a longitudinal direction of the support portion and on which the counterweight is mounted, and a driving part configured to move the movable portion in the longitudinal direction of the support portion.

3. The medical stand of claim 2, wherein the driving part includes:

a driving motor provided on the support portion;

a lead screw connected to a driving shaft of the driving motor; and a screw nut provided on the movable portion and threaded onto the lead screw.

4. The medical stand of claim 2, wherein the driving part includes:

a driving motor provided on the support portion;

a ball screw connected to a driving shaft of the driving motor; and a ball nut provided on the movable portion and threaded onto the ball screw.

5. The medical stand of claim 1, wherein the variable balancing arm includes:

a first balancing arm connected to any one of the second link and the third link, a length of the first balancing arm being variable in accordance with the control signal; and a second balancing arm connected to the remaining one of the second link and the third link and having a constant length.

6. The medical stand of claim 1, further comprising a base configured to install the medical stand at a fixed position, wherein the counter-spring includes a first counter-spring connected at one end of the first counter-spring to the fourth link and connected at the other end of the first counter-spring to the base.

7. The medical stand of claim 6, wherein the counter-spring further includes a second counter-spring connected at one end of the second counter-spring to the third link and connected at the other end of the second counter-spring to the base.

8. The medical stand of claim 1, wherein the controller is configured to adjust the length of the variable balancing arm based on at least one of a position, a number, or an elastic modulus of the counter-spring.

9. The medical stand of claim 1, further comprising:

a base configured to install the medical stand at a fixed position; and a hinge configured to pivotably connect the second link and the third link and provided on the base.

10. The medical stand of claim 9, wherein the detector is provided on the hinge to detect a displacement of at least one of the second link or the fourth link.

11. The medical stand of claim 9, wherein the detector is provided on the hinge to detect an angle between the second link and the fourth link.

12. The medical stand of claim 1, further comprising:

a fifth link parallel to the fourth link;

a sixth link configured to connect the fifth link to a connecting portion for connecting the mounting arm, the first link and the fourth link;

a seventh link configured to connect the fifth link to a connecting portion for connecting the second link and the fourth link, the seventh link being parallel to the sixth link;

an eighth link parallel to the sixth link, the eighth link being connected to a distal end of the mounting arm; and a ninth link configured to connect the eighth link to a connecting portion for connecting the fifth link and the sixth link.

13. The medical stand of claim 12, further comprising a base configured to install the medical stand at a fixed position, wherein the seventh link is fixed to the base.

* * * * *